US011087880B1

(12) United States Patent
Shah et al.

(10) Patent No.: US 11,087,880 B1
(45) Date of Patent: Aug. 10, 2021

(54) MACHINE MODEL GENERATION SYSTEMS AND METHODS

(71) Applicant: Express Scripts Strategic Development, Inc., St. Louis, MO (US)

(72) Inventors: Pritesh J. Shah, Paramus, NJ (US); Christopher Markson, Hawthorne, NJ (US); Logan R. Meltabarger, St. Charles, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 1056 days.

(21) Appl. No.: 15/655,647

(22) Filed: Jul. 20, 2017

Related U.S. Application Data

(63) Continuation-in-part of application No. 15/498,048, filed on Apr. 26, 2017.

(60) Provisional application No. 62/327,994, filed on Apr. 26, 2016.

(51) Int. Cl.
*G16H 50/20* (2018.01)
*G06Q 50/22* (2018.01)
*G16H 10/60* (2018.01)
*G06N 20/00* (2019.01)

(52) U.S. Cl.
CPC ............. *G16H 50/20* (2018.01); *G06N 20/00* (2019.01); *G06Q 50/22* (2013.01); *G16H 10/60* (2018.01)

(58) Field of Classification Search
CPC ........ G16H 50/20; G16H 10/60; G06N 20/00; G06Q 50/22
See application file for complete search history.

(56) References Cited

U.S. PATENT DOCUMENTS

| | | | |
|---|---|---|---|
| 5,664,109 A | 9/1997 | Johnson et al. | |
| 5,801,697 A | 9/1998 | Parikh et al. | |
| 6,112,986 A | 9/2000 | Berger | |
| 7,617,203 B2 * | 11/2009 | Awadallah | ............ G06Q 30/02 |
| 7,756,726 B2 | 7/2010 | Thuerk | |

(Continued)

OTHER PUBLICATIONS

Aspect-Oriented Sentiment Analysis of Customer Reviews Using Distant Supervision Techniques Jürgen Broß (Year: 2013).*

(Continued)

*Primary Examiner* — Kakali Chaki
*Assistant Examiner* — Ababacar Seck
(74) *Attorney, Agent, or Firm* — The Small Patent Law Group LLC

(57) ABSTRACT

A method includes defining model attributes of an organizational machine model that organizes feedback data from one or more sources of the feedback data into plural different topic groups based on similarities in concepts expressed in the feedback data. The model attributes represent criteria for establishment of the organizational machine model and include a topic model number that defines how many of the different topic groups are to be created by the organizational machine model and used to organize the feedback data into, a hyperparameter optimization alpha value that defines how likely a feedback datum in the feedback data is to be included in a single topic group of the different topic groupings or multiple topic groups of the different topic groupings, and a hyperparameter optimization beta value that defines how broadly each of the different topic groups are defined relative to the feedback data.

15 Claims, 10 Drawing Sheets

(56) References Cited

U.S. PATENT DOCUMENTS

| | | | |
|---|---|---|---|
| 7,761,480 B2 * | 7/2010 | Toledano | H04L 63/10 |
| | | | 707/804 |
| 8,275,850 B2 | 9/2012 | Kohan et al. | |
| 8,666,926 B1 | 3/2014 | Nease et al. | |
| 8,818,788 B1 | 8/2014 | Mihalik et al. | |
| 9,268,906 B2 | 2/2016 | Curran et al. | |
| 9,319,449 B2 | 4/2016 | Harpster | |
| 9,426,051 B2 | 8/2016 | Chakrabarti et al. | |
| 2004/0122656 A1 | 6/2004 | Abir | |
| 2007/0223699 A1 | 9/2007 | Jones et al. | |
| 2008/0046292 A1 | 2/2008 | Myers | |
| 2009/0119275 A1 | 5/2009 | Chen | |
| 2010/0010968 A1 | 1/2010 | Redlich | |
| 2012/0179752 A1 | 7/2012 | Mosley | |
| 2013/0187926 A1 | 7/2013 | Silverstein | |
| 2013/0232263 A1 | 9/2013 | Kelly | |
| 2015/0189086 A1 | 7/2015 | Romano | |
| 2016/0259844 A1 * | 9/2016 | Trapeznikov | G06F 16/285 |
| 2017/0250959 A1 | 8/2017 | Gordon et al. | |
| 2017/0323065 A1 * | 11/2017 | Proctor Beauchamp | G06N 20/00 |
| 2018/0253650 A9 * | 9/2018 | Liang | G06N 20/00 |

OTHER PUBLICATIONS

Hyperparameter optimization with approximate gradient Pedregosa (Year: 2016).*

Structured Topic Models for Language Hanna M. Wallach (Year: 2008).*

Auto-WEKA: Combined Selection and Hyperparameter Optimization of Classification Algorithms (Year: 2013).*

Structured Topic Models: Jointly Modeling Words and Their Accompanying Modalities (Year: 2009).*

LDA-Based Document Models for Ad-hoc Retrieval Wei et al. (Year: 2006).*

Proposal of LDA-based Sentiment Visualization of Hotel Reviews Chen et al. (Year: 2015).*

* cited by examiner

MACHINE MODEL GENERATION SYSTEMS AND METHODS

CROSS-REFERENCE TO RELATED APPLICATION

This application is a continuation-in-part of U.S. patent application Ser. No. 15/498,048, which was filed 26 Apr. 2017; said application Ser. No. 15/498,048 claims the benefit and priority of U.S. application 62/327,994, which was filed on 26 Apr. 2016; the entire disclosures of which are incorporated herein by reference.

FIELD

The present disclosure generally relates to medical data processing and more particularly to medical data processing by generating machine model systems.

BACKGROUND

Consumers provide feedback through a wide variety of channels, such as social media, vendor websites, vendor call centers, mobile applications, and online stores for mobile applications. The feedback typically is not centrally available, and may be in a wide variety of formats, syntaxes, etc. Additionally, different consumers may use different words or phrases to provide feedback regarding the same topic.

Consumer feedback can be valuable for a vendor to track and analyze to identify specific or widespread issues with products or services provided by the vendor. Due to the diverse sources of feedback providing the data in an unstructured manner and/or different consumers using different words or phrases to explain the same feedback, analysis of the consumer feedback can be difficult and/or time consuming. For example, it can be difficult to automatically categorized feedback in a commercially reasonable time based on isolated words in the feedback from different sources of the feedback.

The background description is provided for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

BRIEF SUMMARY

In one embodiment, a method includes defining model attributes of an organizational machine model that organizes feedback data from one or more sources of the feedback data into plural different topic groups based on similarities in concepts expressed in the feedback data. The model attributes represent criteria for establishment of the organizational machine model and include a topic model number that defines how many of the different topic groups are to be created by the organizational machine model and used to organize the feedback data into, a hyperparameter optimization alpha value that defines how likely a feedback datum in the feedback data is to be included in a single topic group of the different topic groupings or multiple topic groups of the different topic groupings, and a hyperparameter optimization beta value that defines how broadly each of the different topic groups are defined relative to the feedback data. The method also includes generating the organizational machine model using the model attributes that are defined and the feedback data, and applying the organizational machine model to the feedback data to divide different portions of the feedback data into the different topic groups based on contents of the feedback data, the topic model number, the hyperparameter optimization alpha value, and the hyperparameter optimization beta value.

In one embodiment, a tangible and non-transitory computer-readable storage medium is provided. The medium includes instructions that direct one or more computer processors to define model attributes of an organizational machine model that organizes feedback data from one or more sources of the feedback data into plural different topic groups based on similarities in concepts expressed in the feedback data. The model attributes represent criteria for establishment of the organizational machine model and including a topic model number that defines how many of the different topic groups are to be created by the organizational machine model and used to organize the feedback data into, a hyperparameter optimization alpha value that defines how likely a feedback datum in the feedback data is to be included in a single topic group of the different topic groupings or multiple topic groups of the different topic groupings, and a hyperparameter optimization beta value that defines how broadly each of the different topic groups are defined relative to the feedback data. The instructions also direct the one or more processors to generate the organizational machine model using the model attributes that are defined and the feedback data, and apply the organizational machine model to the feedback data to divide different portions of the feedback data into the different topic groups based on contents of the feedback data, the topic model number, the hyperparameter optimization alpha value, and the hyperparameter optimization beta value.

In one embodiment, a method includes defining model attributes, receiving a topic model number selection, and generating a machine model using a defined default parameter and based on the model attributes that are and the topic model number selection that received. The machine model that is generated is configured to automatically identify topic groupings of feedback data provided to a service provider from one or more data sources based on similarities in concepts conveyed in the feedback data. The method also includes generating a display based on the machine model that is generated.

In one embodiment, a system includes a data manager device that includes one or more processors configured to receive feedback data containing confidential medial information from plural different sources via one or more computer networks. The one or more processors of the data manager device are configured to define model attributes of an organizational machine model that organizes feedback data from one or more sources of the feedback data into plural different topic groups based on similarities in concepts expressed in the feedback data. The model attributes represent criteria for establishment of the organizational machine model and including a topic model number that defines how many of the different topic groups are to be created by the organizational machine model and used to organize the feedback data into, a hyperparameter optimization alpha value that defines how likely a feedback datum in the feedback data is to be included in a single topic group of the different topic groupings or multiple topic groups of the different topic groupings, and a hyperparameter optimization beta value that defines how broadly each of the different topic groups are defined relative to the feedback data. The one or more processors of the data manager device also are configured to generate the organizational machine model using the model attributes that are defined and the feedback data, and to apply the organizational machine model to the feedback data to divide different portions of the feedback data into the different topic groups based on contents of the feedback data, the topic model number, the hyperparameter optimization alpha value, and the hyperparameter optimization beta value.

Further areas of applicability of the present disclosure will become apparent from the detailed description, the claims and the drawings. The detailed description and specific examples are intended for purposes of illustration only and are not intended to limit the scope of the disclosure.

DETAILED DESCRIPTION

Figure 1:
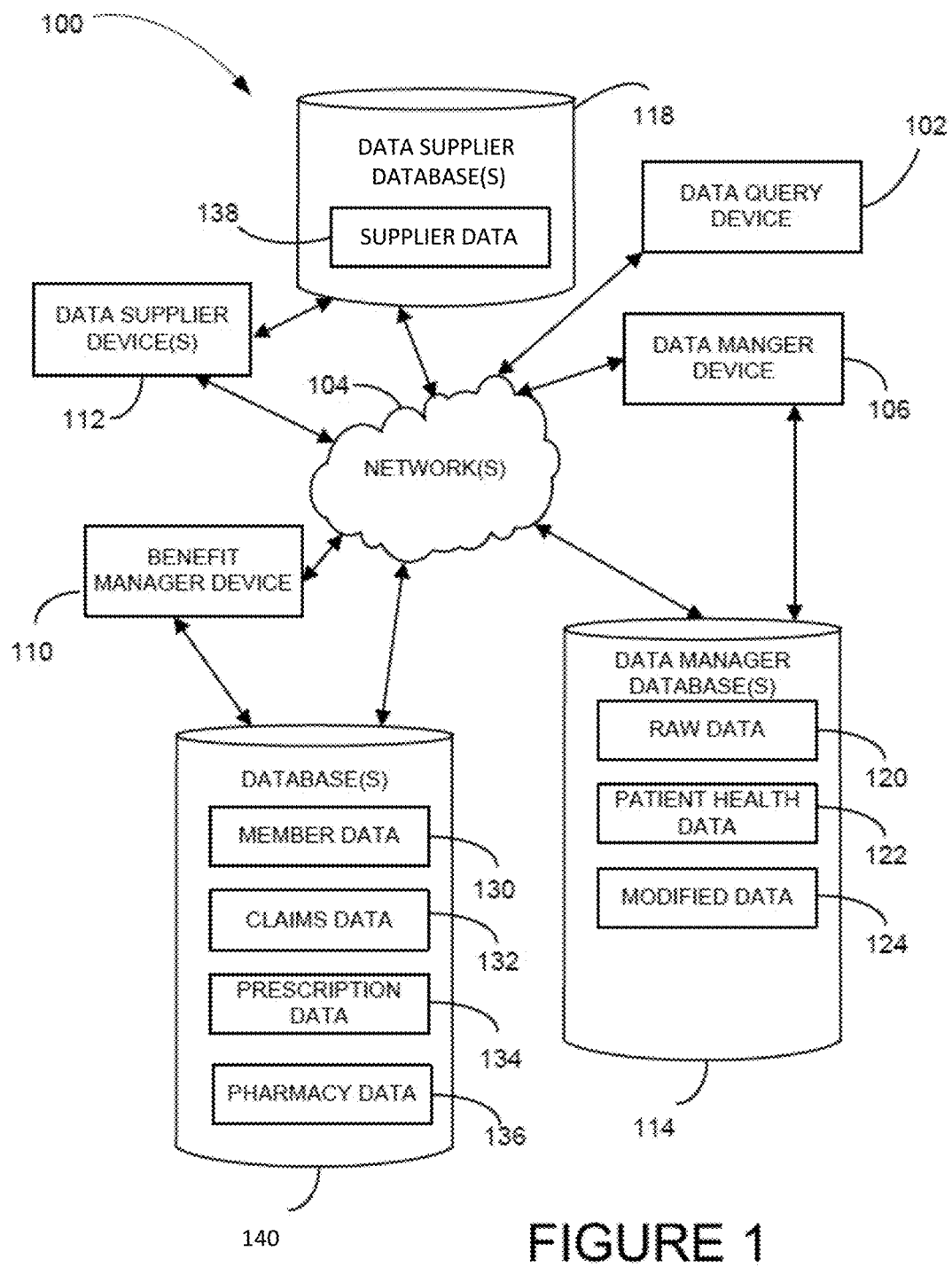
FIG. 1 illustrates one embodiment of a medical processing system.

Example methods and systems for generating machine models used to analyze feedback data are provided. The machine models can be relationships between concepts expressed in feedback data provided from various different sources about a provider of services or products, such as a pharmacy benefit manager, a pharmacy, or the like. The machine models can be automatically learned by computing systems specially programmed to examine the feedback data, determine concepts expressed in the feedback data, and arrange the feedback data into different topic groups. The models can be used for automatic analysis of feedback provided to a service provider for identifying common or widespread issues with products or services.

The machine models can be used to automatically allocate different portions of the feedback data into different topic groupings based on concepts conveyed in the feedback data. The machine models can be used to automatically generate displays to visually present the prevalence of various concepts appearing in the feedback data in a manner that assists users in determining what complaints are appearing most often in the feedback, regardless of the syntax, format, speech pattern, or other way that feedback conveying the same or similar concepts may be provided or recorded. The machine models can be created and saved for later use, thereby allowing the machine models to automatically update the visual displays when new or updated feedback data is available and without having to re-create the machine models.

The methods and systems described herein can allow for varied feedback from a multitude of sources to be quickly and efficiently organized and presented to users within a time period that is significantly faster than manual organization of the information. For example, manual examination and organization of the feedback data as described herein may not be able to be completed before new or updated feedback data is received, thereby rendering the partially completed examination and organization of the feedback data obsolete. Moreover, because different sources of feedback may provide the feedback data in different formats and because persons supplying the feedback may use different syntaxes or phrases to express the same concepts, identifying common topics throughout the feedback from different sources can be difficult to accomplish in a commercially reasonable timeframe. The systems and methods described herein can allow for the topics expressed throughout the feedback in different formats and syntaxes, and from different sources, to be quickly identified so that the feedback can be intelligently analyzed for topics or problems that are trending upward or down. This can assist users of the systems and methods to fix issues to avoid continued negative feedback. Additionally, the systems and methods described herein allow for the customization of how the topics are automatically identified by permitting users to define attributes of models used to identify the topics. These attributes can permit the users to define how many topics are to be identified, how closely related different expressions in the feedback need to be in order to be included in the same topic, whether the feedback is to be modified by applying an ontology for improved determination of the different topics, etc.

FIG. 1 illustrates one embodiment of a medical processing system 100. The system 100 is an example embodiment in which machine models used in the organization and analysis of feedback data can be performed. The system 100 includes a data query device 102 in communication with a data manager device 106 over or via a network 104. As described below, the data manager device 106 controls feedback information supplied or otherwise obtained from one or more sources of the feedback. These sources can be one or more than one service providers, such as a location that provides medications, therapies, or the like. The service provider may provide services, products, or a combination of services and products to customers. Examples of the sources include data supplier devices 112, data supplier databases 118, benefit manager devices 110, and/or databases 140 of the benefit manager devices 110. The data manager device 106 can obtain source data (that represents consumer feedback) from one or more of these sources via the network 104. The data manager device 106 can store at least some of the source data in a data manager database 114 as raw data 120 (source data that is not modified), patient health data 122 (portions of the source data containing confidential information and/or medical information), and/or modified data 124 (source data having the confidential information removed and/or replaced by other information, such as a generic placeholder that does not reveal the confidential information).

At least some of the source data can be obtained from the data supplier devices 112 and/or the database(s) 118 of the data supplier devices 112. This source data also can be referred to as supplier data 138. Examples of the data supplier device(s) 112 include client support centers, customer call centers, message centers, mobile application stores, email servers, text messaging servers, chat room servers, social media website servers, and the like.

Another data supplier device 112 can include the benefit manager device 110. The benefit manager device 110 represents one or more than one device that is operated by an entity at least partially responsible for the management of a drug and/or medical benefit program. While the entity operating the benefit manager device 110 is typically a pharmacy benefits manager, other entities may operate the benefit manager device 110 either on behalf of themselves, the pharmacy benefits manager, or another entity. In some embodiments, the benefit manager that provides the drug benefit may also provide one or more than one additional benefits including a health benefit, a dental benefit, a vision benefit, a wellness benefit, a radiology benefit, a pet care benefit, an insurance benefit, a long-term care benefit, a nursing home benefit, and the like. The source data provided by or otherwise obtained from the benefit manager device 110 can be referred to as benefit data.

The benefit manager device 110 may provide certain member data 130, claims data 132, prescription data 134, and/or pharmacy data 136 from the database 118 for storage as part of source data. The member data 130 may include information regarding members of a pharmacy benefit plan and/or patients of one, or more than one, pharmacy. The member population may be for a single pharmacy benefit plan (e.g., offered on behalf of a single company), or may for multiple pharmacy benefit plans. In general, the member data 130 may include member name, member contact information (e.g., address, telephone number, email address, and the like), and a client identifier that identifies the client associated with the member and/or a member identifier that identifies the member to the client. Various information in the data manager database 114 may be restricted patient health information, e.g., names, dates, drug names, addresses, telephone numbers, and the like.

The claims data 132 includes information regarding pharmacy claims adjudicated by the pharmacy benefit manager under a drug benefit program provided by the pharmacy benefit manager for one, or more than one, clients. In general, the claims data 132 may include client data (e.g., including an identification of the client that sponsors the drug benefit program under which the claim is made, company name, company address, contact name, contact telephone number, contact email address, and the like), an identification of the member that purchased the prescription drug giving rise to the claim, the prescription drug that was filled by the pharmacy (e.g., the national drug code number), the dispensing date, generic indicator, number, medication class, the cost of the prescription drug provided under the drug benefit program, the copay/coinsurance amount, rebate information, and/or member eligibility. The claims data 132 may also include claims adjudicated for healthcare related services other than prescriptions filled under a drug benefit program. Examples of other healthcare related services may include medical services (such as treatment, screening services, laboratory services and the like), dental related services, and vision care related services. Additional information may be included in the various claims of the claims data 132. Various information in the claims data 132 may be restricted patient health information, e.g., names, dates, drug names, medical services, amounts, pharmacy information, and the like.

The prescription data 134 may include information regarding prescriptions that may be issued by providers on behalf of patients, who may be members of the drug benefit plan, for example to be filled by a pharmacy. Examples of the prescription data 134 include patient names, medication or treatment (such as lab tests), dosing information, and the like. The prescriptions may be electronic prescriptions, paper prescriptions that have been scanned, or otherwise turned into data that can be stored in an electronic database as described herein. In some embodiments, the dosing information reflects a frequency of use (e.g., once a day, twice a day, before each meal, etc.) and a duration of use (e.g., a few days, a week, a few weeks, a month, etc.). Various information in the prescription data 134 may be restricted patient health information, e.g., names, dates, drug names, dosage, test results, medical services, amounts, pharmacy information, and the like.

The pharmacy data 136 may include information regarding pharmacies. The pharmacy data may include, by way of example, national provider identifier information associated with the pharmacies, location data regarding the location of the pharmacies, information data regarding the pharmacy hours and/or telephone number, pharmacy network association data defining the pharmacy network associations of which the pharmacies are associated, and the like. Various information in the pharmacy data 136 may be restricted patient health information, e.g., pharmacy information, and the like.

The data supplier data 138 as may be stored in the database 118 may include the member data 130, the claims data 132, clinical data, provider data, drug data, the prescription data 134, and/or the pharmacy data 136. The member data 130 and the claims data 132 may be for a same member population as maintained by the benefit manager operating the benefit manager device 110, or for a different population. In some embodiments, the source data is stored separately from the member data 130, claims data 132, and/or data supplier data 138. Various information in the data supplier data 138 may be restricted patient health information.

The clinical data may include clinical records regarding member diagnosis and/or therapy. The clinical data may be obtained from hospitals, medical insurance companies, drug trials, medical laboratories in the form of clinical records and/or the member via online questionnaires, for example. In some embodiments, the clinical data includes medical claims and/or lab data. The clinical data can include medication data, such as information about a claim made under the medical benefit instead of the prescription drug benefit. Various information in the clinical data may be restricted patient health information. This restricted patient health information is information that must be removed or redacted to comply with medical data rules, regulations, and/or laws. Optionally, restricted information can include information that a person (e.g., the patient) has requested be kept confidential (except for one or more individuals selected by the patient), even if the information is not required to be removed or redacted to comply with rules, regulations, or laws.

The devices 102, 106, 110, 112 represent hardware circuitry that includes and/or is connected with one or more than one processor, such as one or more than one microprocessor, field programmable gate array, integrated circuit, or the like. Examples of the devices 102, 106, 110, 112 include a set-top box (STB), a receiver card, a mobile telephone, a personal digital assistant (PDA), a display device, a portable gaming unit, and a computing system; however other devices may also be used. For example, the devices 102, 106, 110, 112 may include a mobile electronic device, such an IPHONE or IPAD device by Apple, Inc., mobile electronic devices powered by ANDROID by Google, Inc., and a BLACKBERRY device by Blackberry Limited. The devices 102, 106, 110, 112 may also include other computing devices, such as desktop computing devices, notebook computing devices, netbook computing devices, gaming devices, and the like. Other types of electronic devices may also be used. When instructions for the present methods are loaded into one or more of the example systems, the device 102, 106, 110, or 112 can be specifically dedicated or programmed to perform the operations described herein. Other circuitry may also perform that present methods.

One or more than one of the devices 102, 106, 110, 112 communicate via the network 104. The network 104 can include one or more than one computerized communication network. Examples of the network 104 include a Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 can also include optical communications. Other wired and wireless networks may also be used. In some embodiments, the network 104 can include proprietary network communication technologies such as secure socket layers (SSL) technology, technology found in a prescribing network (e.g., the electronic prescribing network operated by Surescripts of Arlington, Va.), and the like.

Figure 2:
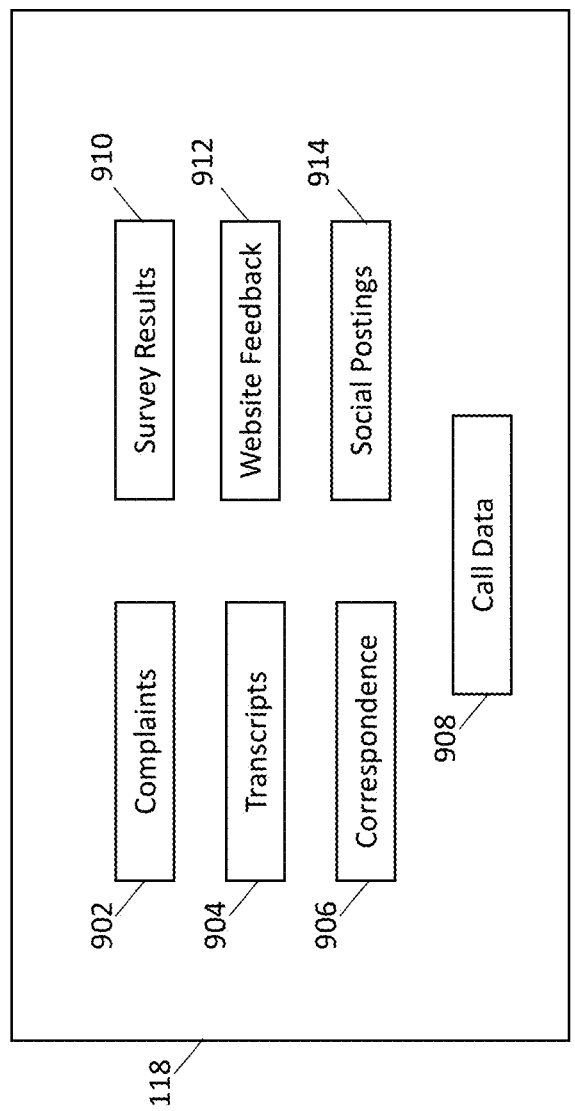
FIG. 2 illustrates one example of a database shown in FIG. 1 that can be maintained by a source of feedback data.

FIG. 2 illustrates one example of the database 118 that can be maintained by a source of the source data. The database 118 can store one or more types of source data that is accessible by the data supplier devices 112 for communication to the data manager device 106 via the network 104. The database 118 can store a variety of information that represents feedback concerning services, products, experiences, or the like. The wide variety of sources and types of feedback can make it difficult to identify topics within the feedback and/or to organize different portions of the feedback into the different topics. For example, the same displeasure with a common service can be expressed differently by persons to different sources and/or can be expressed using different phrases, syntaxes, data formats, etc.

Examples of the source data include complaint data 902 ("Complaints" in FIG. 2), which can represent recorded information on internal employee complaints or feedback, such as emails, surveys, completed website forms, or the like, through which employees can provide complaints regarding company services or the like. Another example of source data is transcript data 904 ("Transcripts" in FIG. 2), which represents written transcriptions of verbally communicated information. Examples of the transcript data 904 include transcripts of telephone calls pharmacy benefit manager or another entity, transcripts of chat sessions, etc. Another example of source data is correspondence data 906 ("Correspondence" in FIG. 2), which represents written correspondence to or from one or more persons. Examples of the correspondence data 906 include emails, text messages, scanned copies of hardcopy correspondence, or other electronic correspondence.

Another example of source data is call data 908, such as dates and/or times of phone calls, phone numbers, area codes (without the remainder of the phone number), or the like, associated with received phone calls. Survey results 910 represents another example of source data, and can include patient satisfaction data regarding various programs and services offered by the pharmacy benefit manager or other supplier. The patient or member may be asked about their use of and satisfaction with a specific service, e.g., home delivery, member services, participating pharmacy program, and/or a specialty pharmacy program. The survey may target a random sample of members who have filled a prescription, used received medical treatment, or contacted a contact center in the prior two weeks. The survey may record their satisfaction on a scale range (e.g., one to five, one to ten, or the like). There are multiple sub-sources that may use the survey, including but not limited to, a call/contact center, home delivery pharmacy, retail pharmacy, and specialty pharmacy. Another survey may be an employee feedback on aspects of home delivery, from placing their order, communications they received and interactions they had with the home delivery team.

Another example of source data is website feedback 912, which represents data indicative of user feedback provided to websites, user rankings of websites, and the like. This data may be obtained from a mobile app store, the website itself, the hosting service of the website, etc. The source data can include social media posts 914 ("Social Postings" in FIG. 2). This data can include postings on one or more social media websites or mobile apps that are accessible. For example, the social media posts 914 can be postings on FACEBOOK, TWITTER, LINKEDIN, or the like, that refer to the pharmacy benefit manager or another entity.

The source data can be updated over a designated time period or other time period. For example, one or more portions of the source data can be updated on a real-time basis, or as new feedback is provided to the source associated with the updated source data. As another example, one or more portions of the source data can be periodically updated and/or updated on-demand, such as when an operator or user (at or using the source) requests that the feedback data associated with the source be updated.

The source data may also include information relating to escalation(s) to senior management within the company or pharmacy benefit manager. The escalations data is typically worked by a small team where the team works to resolve a concern of a patient, identify a root cause or opportunity, and ensure that solutions are in place to avoid future occurrences of the concern.

The data may also include social media data. The specialty social media teams and systems monitor social media, e.g., FACEBOOK, TWITTER, CONSUMER AFFAIRS, blogs, forums and YELP, to develop and input social media data into the databases. Such social media data may also develop complaint requests to the escalation team or compliments to the escalations team. Other types of input may be email, voicemail, and calls from a member. The data may be website feedback. The website feedback may be input into a device by a member via a member website (e.g., at www.express-scripts.com), e.g., at a "tell us about your experience" link, which may be part of a "Contact Us" page. A patient or member provides their net promoter score on how likely the patient or member is to recommend EXPRESS SCRIPTS to friends and family and provide comments related to their score.

Optionally, the source data (e.g., the benefit data) can include information regarding prescribers, pharmaceutical manufacturers, prescription drugs, prescription drug average wholesale price, co-pays, clients of a pharmacy benefits manager, and the like. In some embodiments, the source data can be developed through analysis performed by the data supplier device 112 or by a person or organization that operates the data supplier device 112. In some embodiments, the source data may be developed by a single organization, or multiple organizations, and provided to the data supplier device 112. The source data developed or obtained by the data supplier device 112 need not be related to prescription drugs, but can be from one, or more than one, data categories of interest to the data manager device 106. In some embodiments, the data supplier operating the data supplier device 112 is a client of the pharmacy benefits manager operating the benefit manager device 110 and/or a client of the data manager operating the data manager device 106. In some embodiments, the data supplier operating the data supplier device 112 is a governmental organization. In an example, the data from the data supplier device 112 may also be data that is restricted from sharing outside a protected health data secure or compliant system or device.

The data manager device 106 can examine the source data to determine whether the source data includes confidential information. This examination can be performed by the data manager device 106 parsing the information in the source data by breaking apart the source data into distinct parts of sentences (e.g., object words, verbs, nouns, subject words, adjectives, adverbs, etc.), and comparing the parsed information to one or more than one list, table, or other memory structure containing designated confidential information. The designated confidential information can be words, phrases, numbers, dates, etc., that are previously identified and labeled as confidential information. For example, a list of various given names, last names, medical conditions, medications, dates, or the like, can be used to by the data manager device 106 to identify confidential information. If a word or phrase appearing in the source data matches or is similar to the identified confidential information, then the word or phrase is identified by the data manager device 106 to be confidential information.

Responsive to identifying confidential information in the source data, the data manager device 106 can remove the confidential information from the source data. This version of the source data can be referred to as the modified data 124 shown in FIG. 1. The modified data 124 can include the non-confidential information and contextual placeholders in place of the confidential information. A contextual placeholder is a label of a category or type of confidential information that does not disclose the specific details of the confidential information. For example, [NAME] can be used as a contextual placeholder in the modified data to replace a customer's name, [DATE] can be used as a contextual placeholder in the modified data to replace a date, [MEDICAL INFO] can be used as a contextual placeholder in the modified data to replace a medical condition, medication, or medical diagnosis, [CLIENT NAME] can be used as a contextual placeholder in the modified data to replace the name of a client of a pharmacy benefit manager, [FINANCIAL INFO] can be used as a contextual placeholder in the modified data to replace an account number, social security number, bank name, or the like.

The data manager device 106 can store the source data from the supplier devices 112 and/or benefit manager device 110 as the raw data 120 in the data manager database 114. A copy of the raw data 120 that includes the confidential information can be stored in the data manager database 114 as the patient health data 122. Optionally, the copy of the raw data 120 that includes confidential information, but not necessarily confidential patient health data, can be stored in the data manager database 114 as the patient health data 122. The modified or de-identified data having the confidential information replaced with the contextual placeholders can be stored by the data manager device 106 in the data manager database 114 as the modified data 124. The feedback data used to create the machine models can be obtained from the modified data 124 and/or the raw data 120. Optionally, the feedback data used to create the machine models can include the patient health data 122.

The data manager device 106 can generate one or more than one machine models that are used to automatically identify topic groupings of feedback data provided to one or more than one source (e.g., service providers) based on similarities in the concepts conveyed in the feedback data. The machine model can be used as or used in a software application that can operate independent of the data manager device 106 (e.g., the application can operate on another computing device) or that operates on the data manager device 106 (e.g., to direct operations of the data manager device 106). The machine model can be used to automatically determine conceptual models of relationships between concepts set forth in the feedback data from sources.

A concept is a common idea or theme that is the subject of different complaints, compliments, or other types of feedback. Depending on how the concepts in the feedback data are grouped together into topic groups or groupings, the same feedback data can express the same or different concepts. An example set of feedback data from one or more than one source can include a complaint about a picture on a website not loading on a display, a compliment on the layout of the same website, a complaint about the same website repeatedly crashing, a complaint about payment not going through the same website, and a complaint about the customer service number listed on the website not being correct. If a topic grouping of concepts is broadly defined, such as concepts related to the same website, then all of the feedback data in the example set can be grouped by the machine model into the same website topic grouping because all the complaints and compliments relate to the same website.

But, such a broad grouping of concepts may not be helpful to identify problems or issues with services or products provided by the sources. Too broad of a definition of the concept in a topic grouping can hide or occlude different problems or issues related to the same broadly defined concept (e.g., a website). For example, a first topic grouping can be functional aspects of a website, a second topic grouping can be customer service, and a third topic grouping can be payment issues. The machine model can then sort the feedback data in the preceding example set among the different topic groupings based on the different and more specific concepts expressed in the feedback data. The complaint about the picture on a website not loading on a display, the complaint about the same website repeatedly crashing, and the compliment on the layout of the same website can be associated by the machine model with the first topic grouping (non-functional aspects of a website), the complaint about the customer service number listed on the website not being correct can be associated by the machine model with the second topic grouping (customer service), and the complaint about payment not going through the same website can be associated by the machine model with the third topic grouping (payment issues).

As described herein, the data manager device 106 can receive or determine attributes of a machine model (that is to be created) and a topic model number selection that indicates how many topic groupings are to be identified in a set of feedback data by the machine model that is to be created. The data manager device 106 can then examine the feedback data in the set to determine relationships between the feedback data, and can determine topic groupings for sorting different portions of the feedback data into based on which concepts are expressed in the feedback data, how the concepts in the different portions of the feedback data are related with each other, etc. The data manager device 106 can create the machine model to sort the feedback data into the various topic groupings, with the current set of feedback data and optionally with new, updated feedback data that is received in the future. The machine model can define the topic groupings that are used by the data manager device 106 (or optionally another computer device) to generate displays for users to determine various features of the feedback data, such as how the topic groupings are related, how prevalent one concept of a topic grouping is in the feedback data relative to other concepts of other topic groupings, etc.

For example, the machine model that is created can be used to examine the feedback data to determine whether many customers are complaining about a website or mobile application service interruption, whether customers are expressing displeasure with the same call center, whether customers are complaining about the cost of a particular product, whether customers are complaining about the same insurance plan not providing benefit coverage for a particular medication, etc. The feedback provided by different persons via diverse sources is unstructured data that can be difficult to examine for analyzing the data. For example, complaints from different persons about a product cost coming from different social media websites, a pharmacy benefit manager website, a mobile application store, and/or a call center can be recorded differently in different data formats and/or syntaxes.

Figure 3:
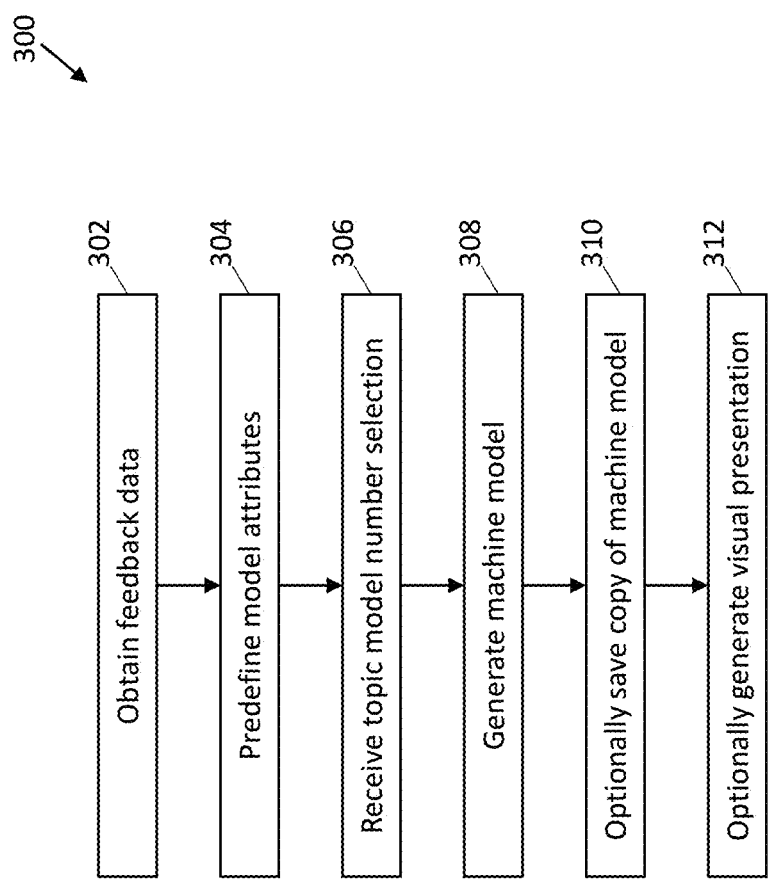
FIG. 3 illustrates a flowchart of a method for generating a machine learning model used in analyzing feedback information.

FIG. 3 illustrates a flowchart of a method 300 for generating a machine model. The flowchart can represent operations performed by the system 100 under the direction of one or more software applications to identify topic groupings in unstructured feedback data obtained from a variety of sources, and create a machine model that can examine the current and future feedback data, group different portions of the feedback data into the topic groupings, and visually present relationships between the different topic groupings.

The method 300 can be used to generate different topic groupings of the machine models. The same data manager device 106 and the same method 300 can be used to identify or define different sets of topic groupings for machine models that examine different sets of feedback data. For example, the same topic groupings may not yield useful information when used to examine different sets of feedback data. While topic groupings related to website and customer service issues may be useful to examine feedback data that includes complaints about website crashes and customer service failures, these topic groupings may be useless or less useful for examining feedback data that includes complaints about payment issues, pharmacies not being able to apply benefits of a managed benefit plan, or the like.

Figure 4:
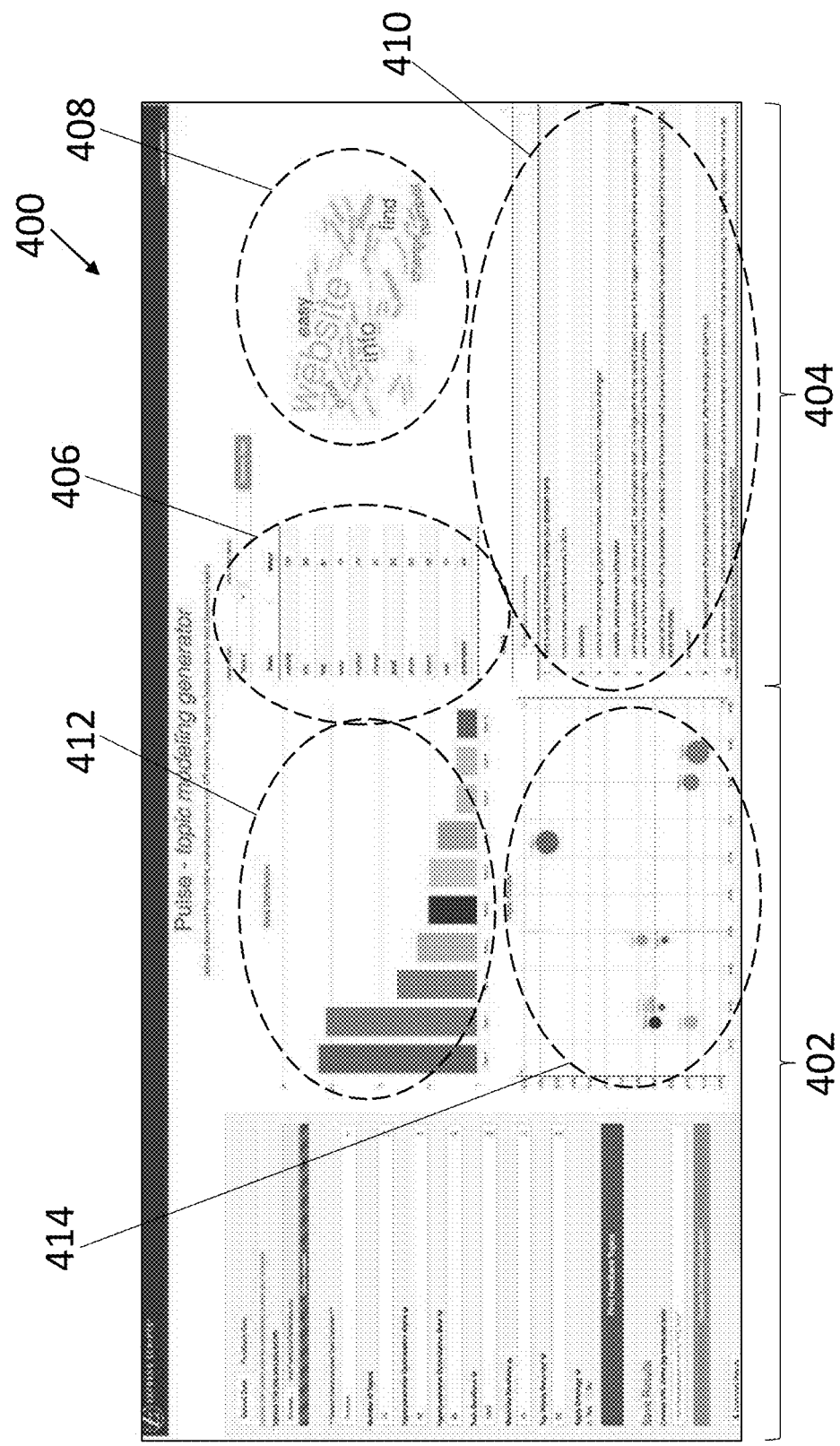
FIG. 4 illustrates one example of an interactive graphical user interface that can be generated by the data manager device shown in FIG. 1 for a display device.
Figure 5:
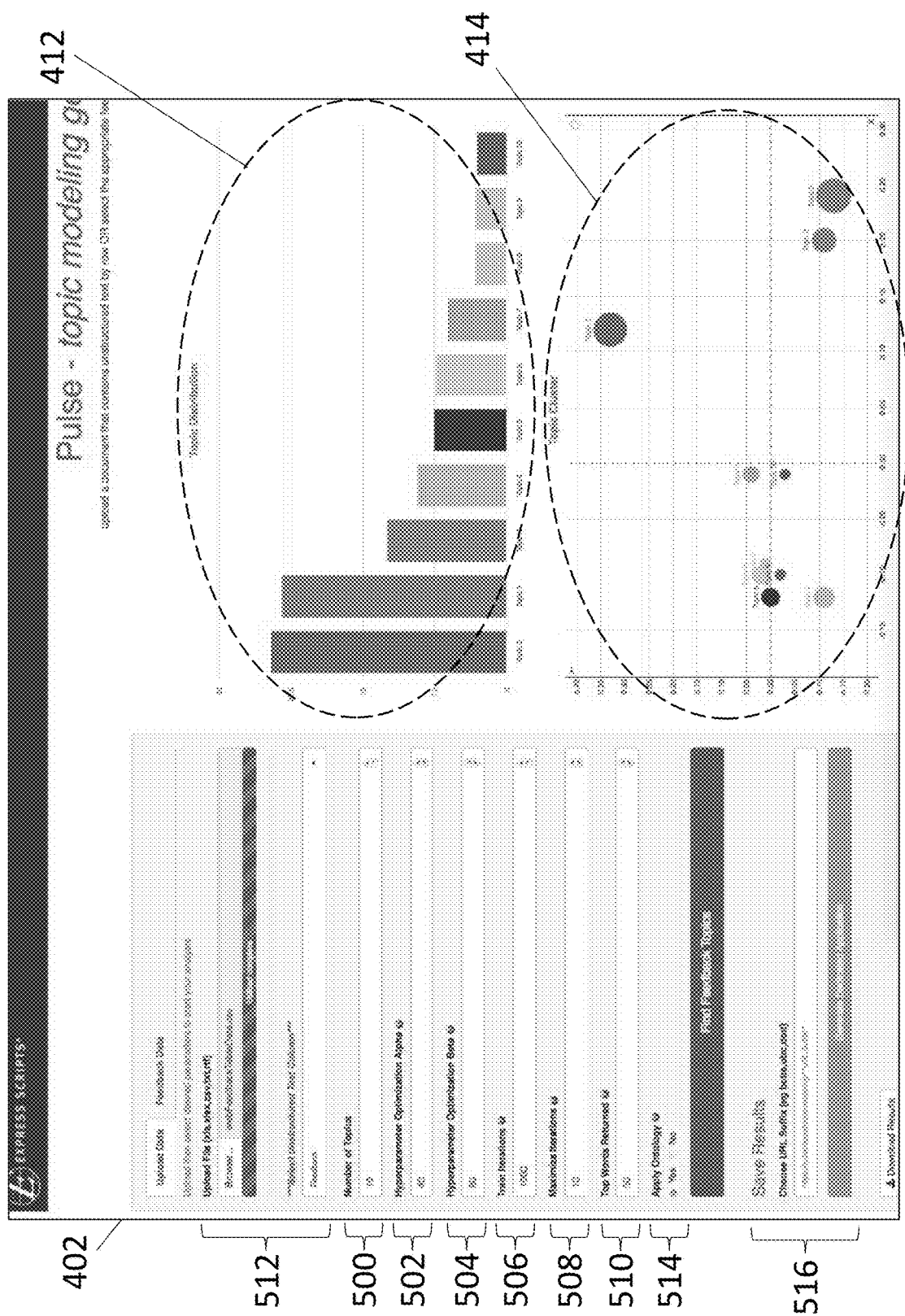
FIG. 5 illustrates one example of a left portion of the interface shown in FIG. 4.
Figure 6:
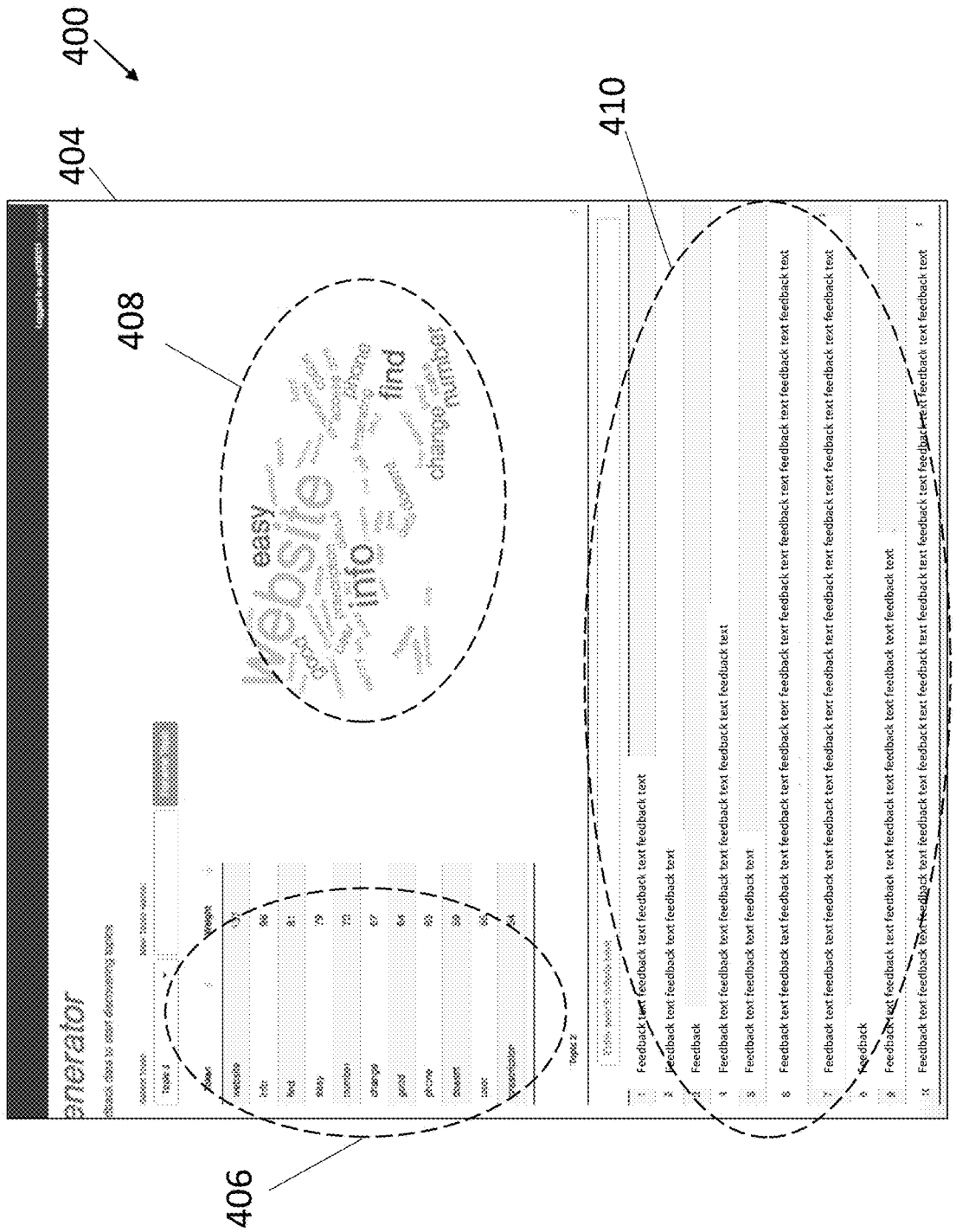
FIG. 6 illustrates one example of a right portion of the interface shown in FIG. 4.

At 302, feedback data to be examined is obtained. The feedback data can be obtained by selecting a source or more than one source of the feedback data, or by uploading feedback data. With continued reference to the flowchart of the method 300 shown in FIG. 3, FIG. 4 illustrates one example of an interactive graphical user interface 400 that can be generated by the data manager device 106 for a display device. The interface 400 can be presented to a user or operator of the data manager device 106 for creation of machine models and/or for viewing the visual presentations of feedback data and topic groupings determined by the machine models. FIG. 5 illustrates one example of a left portion 402 of the interface 400 shown in FIG. 4 and FIG. 6 illustrates one example of a right portion 404 of the interface 400 shown in FIG. 4. FIGS. 6 through 9 illustrate parts of the interface 400 according to numerous examples.

The interface 400 includes a graphical input area 512 that can be used to select a source or more than one source of feedback data. The area 512 can include drop-down menus, clickable or otherwise selectable buttons or icons, text-entry windows, or the like, that a user or operator can employ to select and/or input a source or sources for the feedback data. Optionally, the user or operator can upload feedback data from a file or spreadsheet.

At 304, attributes of a machine model are predefined. The attributes of the machine model can be predefined based on default values and/or based on user input into the data manager device 106. The machine model attributes can be defined via the interface 400 as shown in FIG. 5. The interface 400 includes several graphical input areas 500, 502, 504, 506, 508, 510, 512, 514 that are used to allow an operator or user to input one or more than one machine model attributes. These input areas 500, 502, 504, 506, 508, 510, 512, 514 can include drop-down menus, clickable or otherwise selectable buttons or icons, text-entry windows, or the like.

The input area 502 is used to define a hyperparameter optimization alpha value. A default value for the hyperparameter optimization alpha value optionally can be used (e.g., forty or another number). The hyperparameter optimization alpha value defines how likely a feedback datum is to be included in a single topic grouping or multiple topic groupings. A feedback datum can be a single instance of feedback data, such as a single website comment, a transcription from a single telephone call, or the like. Greater hyperparameter optimization alpha values result in a feedback datum having concepts being more likely to be included in multiple topic groupings while smaller hyperparameter optimization alpha values result in the same feedback datum having concepts being less likely to be included in multiple topic groupings.

The input area 504 is used to define a hyperparameter optimization beta value. A default value for the hyperparameter optimization beta value optionally can be used (e.g., eighty or another number). The hyperparameter optimization beta value defines how likely a topic grouping is to be broadly defined by the machine model. The machine model can define a topic grouping based on a mixture or combination of words, contextual placeholders, etc. For example, depending on the words used in the feedback data being examined, the machine model can define a first topic grouping as feedback data that includes words such as "call center," "customer support," and variations on words expressing time periods (e.g., weeks, hours, days, minutes, etc.). The machine model can define a second topic grouping as feedback data that includes words such as "medication," "prescription," and variations on words expressing availability depending on the words used in the feedback data being examined. The set and/or combinations of words associated with or used to define a topic grouping can be expanded for greater hyperparameter optimization beta values and can be reduced for smaller hyperparameter optimization beta values.

The input area 506 is used to define a training iteration value. The data manager device 106 creates the machine models using machine learning. The data manager device 106 examines the feedback data being examined using the predefined attributes, identifies the concepts expressed by the feedback data, and learns relationships between these concepts. These relationships can be used to determine the topic groups that the feedback data are arranged into. The machine model that is generated represents these relationships and/or topic groupings.

For example, the data manager device 106 can search for sets of predefined words, terms, and/or phrases of interest in the feedback data. Each set of predefined words, terms, and/or phrases can be associated with a different predefined concept. For example, words such as "website," "site," "page," "webpage," and the like, can be a set of words associated with the predefined concept "website." Words and phrases such as "telephone," "call," "customer service," and the like, can be another set of words and phrases associated with the predefined concept "customer service call center." Many other sets of words and phrases associated with different predefined concepts may exist.

The data manager device 106 can examine the contents of the feedback data to determine how many concepts are expressed or included in the same feedback datum. For example, the same feedback datum may express or include several different concepts. The data manager device 106 can select one of these concepts as being a selected concept associated with the feedback datum. The concept that is selected can be based on the hyperparameter optimization alpha value and/or the hyperparameter optimization beta value.

The data manager device 106 can examine the identified concepts in different feedback data and determine relationships between different portions of the feedback data based on what concepts are included in the different portions. For example, feedback data having concepts relating to payment problems, website credit card submission pages, and pharmacy credit card denials can be identified by the data manager device 106 as being related to each other by a first relationship (e.g., payment issues), feedback data having concepts relating to website credit card submission pages, website crashes, and website "404" errors can be identified by the data manager device 106 as being related to each other by a second relationship (e.g., website functional errors), and so on. But, concepts related to pharmacy credit card denials and website "404" errors may not be identified as having a predefined relationship with each other due to the dissimilarity between these concepts. Some concepts can have relationships with multiple other concepts (e.g., website credit card submission pages). The data manager device 106 can examine how often various concepts appear in the feedback data and, for those concepts or sets of concepts appearing more often in different portions of the feedback data, determine that the portions of the feedback data have a relationship with each other (e.g., have related concepts).

For each feedback datum in the set of feedback data being examined, the data manager device 106 can select a first concept during a first training iteration. The data manager device 106 can repeat this selection of concepts for each feedback datum in the feedback data during the first training iteration. Upon selecting a concept for each of the feedback datum in all or a portion of the feedback data, the first training iteration can be completed. The data manager device 106 can experiment with identifying or defining different relationships between selected concepts in different iterations to determine which feedback datum are to be included in the same topic grouping. For example, the feedback data with selected concepts having relationships with each other can be sorted into a first topic grouping, the feedback data with selected concepts having another relationship with each other can be sorted into a second topic grouping, and so on, until the feedback data is divided into all of the topic groupings (defined by the number of topic groupings attribute).

The data manager device 106 can repeat this process one or more additional times up to the number of train iterations input in the area 506 (or up to the default value of the number of train iterations). Each iteration can result in the data manager device 106 grouping different portions of the feedback data in different topic groupings depending on the various different relationships between the selected concepts being defined by the data manager device 106. For example, in another iteration, the data manager device 106 can select a different concept for one or more feedback datum and/or can use a different relationship between selected concepts to group the feedback data differently in the topic groupings. The data manager device 106 can select the results of one of the iterations for presentation to the user or operator, such as an iteration that results in at least a designated threshold number or percentage of the feedback data being placed into a topic grouping or at least a designated threshold number or percentage of the feedback data in each of the topic groupings. The input area 508 is used to define an upper limit on the number of iterations performed by the data manager device 106, as described above. If a value is not input into the area 508, then a default value can be used.

The input area 510 is used to define a limit on the number of words, phrases, or terms of interest that are to be returned for each topic grouping. Depending on the relationships between concepts associated with the topic grouping that are identified by the machine model created by the data manager device 106, a large number of words, phrases, or terms of interest can be associated with a topic grouping. The data manager device 106 can display feedback datum with these words, phrases, or terms of interest highlighted or otherwise displayed differently than other words, phrases, or terms in the feedback datum. If too many words, phrases, or terms of interest are associated with a topic grouping, then the user or operator may have difficulty in seeing the words, phrases, or terms of interest associated with the topic grouping on the interface 400. Therefore, the input area 510 can be used to set an upper limit on the words, phrases, or terms of interest associated with the topic groupings and/or highlighted in the interface 400. Optionally, a default value (e.g., fifty or another value) can be used.

The input area 514 is used to designate whether ontology is to be applied by the data manager device 106 to the feedback data. Ontology is applied to the feedback data to detect correlation between different expressions of the same or similar concepts. Applying the ontology can involve the data manager device 106 searching for and removing special characters from the feedback data. The special characters can be indicia or indicium that are not letters of the alphabet and/or are not numbers. The data manager device 106 can correct spelling in the feedback data by searching for and finding previously identified misspellings of various words or phrases. The data manager device 106 can apply the ontology by reducing the terms appearing in the feedback data. The terms appearing in the feedback data can be reduced by eliminating (or not counting) duplicative entries of the same feedback data (e.g., the exact same feedback provided by the same or diverse sources, including the same letters, words, misspellings, etc.).

The ontology applied by the data manager device 106 can involve identifying correlations between synonyms appearing in the feedback data. Different words or phrases can be used in the feedback information to express the same idea or concept. For example, the words medicine, medication, pills, script, prescription, Rx, etc., can be used in the same or different feedback data to refer to the same idea or concept (e.g., prescribed medicine). The data manager device 106 can store or access a list, table, spreadsheet, or other memory structure, that associates different words or phrases with each other. The associated words can be identified as correlated words or phrases that convey the same or similar meaning. The data manager device 106 can identify correlations between words or phrases in the feedback data by grouping the words or phrases having the same or similar meaning with each other. The data manager device 106 can apply the ontology to the feedback data by replacing correlated words or phrases with a primary word or phrase. With respect to the preceding example, the data manager device can replace all instances of the words medicine, medication, pills, script, prescription, Rx, etc., in the feedback data with "prescribed medicine."

Applying the ontology to the feedback data can resolve many issues that otherwise could prevent or significantly hinder analysis of the unstructured data of the feedback data. Because different persons providing the feedback may use different words or phrases to provide the same meaning, examination of the feedback data (without applying the ontology) may not identify repeated expressions of the same complaint. Additionally, misspellings in the feedback data can prevent the data manager device 106 from identifying repeated expressions of the same complaint.

Returning to the description of the flowchart 300 shown in FIG. 3, at 306, a topic model number selection is received. The topic model number selection is a number of topic groupings to be included in the machine model. The input area 500 can be used to define the number of topic groupings to be included in the machine model. A default value for the number of topic groupings optionally can be used (e.g., ten or another number). The number of topic groupings defines and restricts how many groups the feedback data being examined by the machine model are sorted into.

Too few topic groupings can result in feedback data relating to starkly different concepts being grouped together in the same topic grouping, while too many topic groupings can result in feedback data relating to similar concepts being separated into different topic groupings. As described below, the machine model examines the concepts expressed in a set of feedback data to determine which concepts are more or less similar, and divides the feedback data into the topic groupings based on the defined number of topic groupings and how similar or dissimilar different concepts expressed in the feedback data are. In one embodiment, the machine model is not permitted to create more than the defined number of topic groupings regardless of how dissimilar the concepts in the feedback data.

At 308, the machine model is generated by the data manager device 106. The machine model can be created by identifying the topic groupings of the feedback data based on concepts identified in the feedback data and relationships between the concepts selected for the feedback data by the data manager device 106, as described above. The data manager device 106 can create the machine model using at least one defined default parameter, such as the default value of one or more of the attributes described above. The data manager device 106 also can create the machine model based on the model attributes that are predefined (at 302) and the topic model number that is selected (at 306).

At 310, the machine model that is generated optionally is saved. The interface 400 includes an output area 516 in which the user or operator of the data manager device 106 can input a name or other identifying information. The data manager device 106 can then create an electronic copy of the machine model that was generated. This copy can be a software application that operates on the data manager device 106 or another computing device. The copy can be provided with new or updated feedback data and sort the feedback data into the topic groupings created in the machine model. This can allow for new or updated feedback data to be organized into the topic groupings without having to repeat the operations of defining attributes of the machine model, receiving the topic model number selection, and generating the machine model.

Optionally and in one embodiment, output can be generated by the data manager device 106 based on the machine model. This output can include a control signal that directs a device to perform one or more responsive actions. For example, if the data manager device 106 determines that the machine model identifies one or more topic groupings indicating that a website, portion of a website (e.g., a script or page within the website), mobile application, call center, or the like, is not working or has other problems, the data manager device 106 can generate and communicate a control signal to a computer server to automatically deactivate or reset the website, mobile application, telephone, or the like. This can result in the problem potentially being automatically fixed or prevented from causing further problems until fixed.

At 312, one or more visual presentations of the feedback data optionally are generated based on or using the machine model. Examples of the visual presentations are shown in FIG. 4 with additional details of the presentations viewable in FIGS. 6 through 9. The visual presentations can include a customizable topic grouping list 406 (shown in FIGS. 4, 6, and 7), a word cloud 408 (shown in FIGS. 4 and 6), a feedback data details list 410 (shown in FIGS. 4 and 6), a topic grouping histogram 412 (shown in FIGS. 4 and 8), and a topic cluster graph 414 (shown in FIGS. 4 and 9). One, several, or all of these presentations can be shown by the data manager device 106 instructing an electronic display to show the presentations based on the feedback data and the machine model.

The customizable topic grouping list 406 includes a drop-down list 702 of the different topic groupings identified by the machine model, as well as a prevalence list 704 of words, phrases, or terms of interest that appear often in a topic grouping selected in the list 702. The prevalence list 704 indicates the words, terms, or phrases of interest appearing in the feedback data of the selected topic grouping. These words, terms, or phrases indicate concepts conveyed in the selected topic group. A weight score can be provided for the different words, terms, or phrases in the list 704 to indicate how often the corresponding word, phrase, or term appears in the feedback data.

Figure 7:
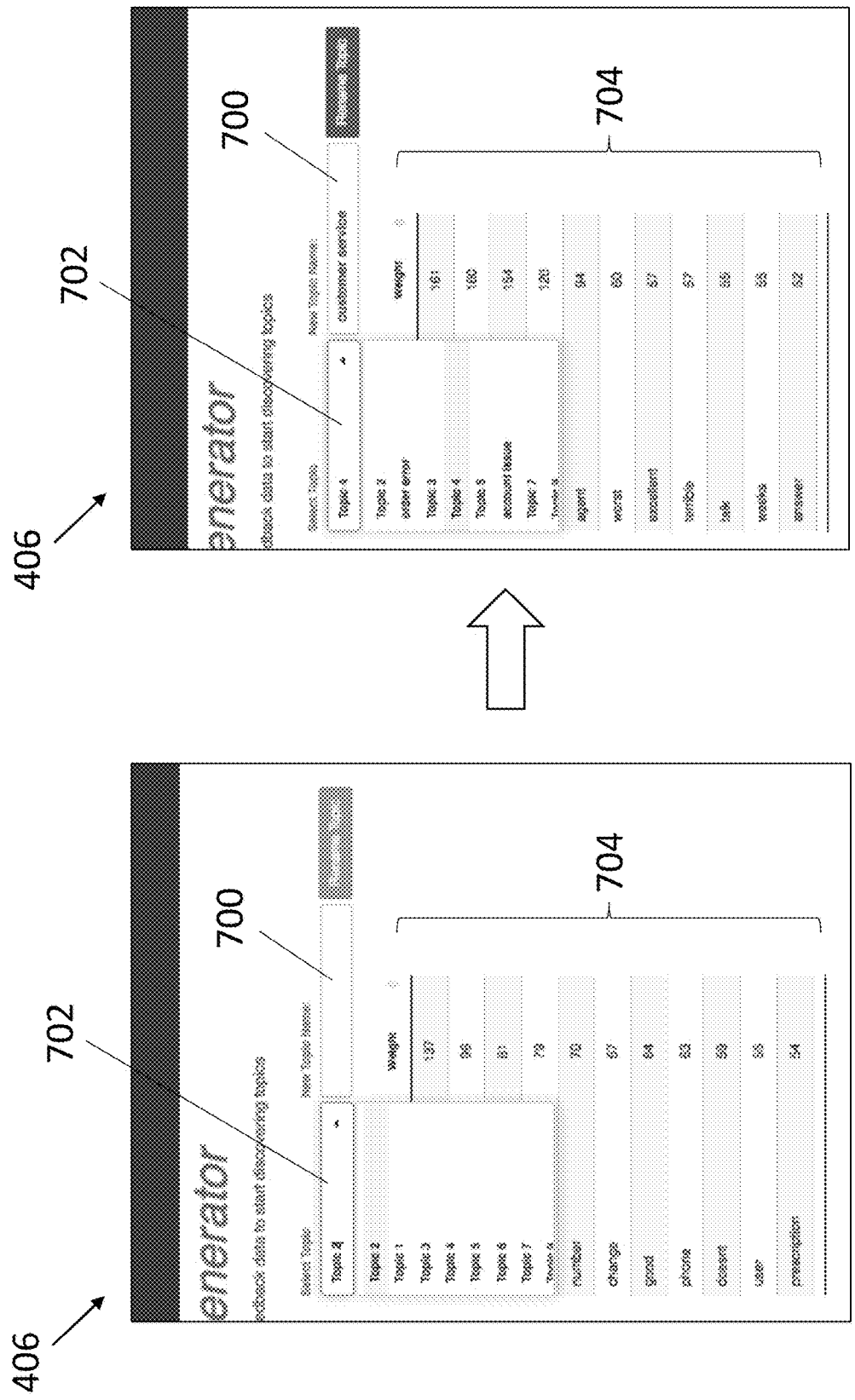
FIG. 7 illustrates another part of the interface shown in FIG. 4.
Figure 8:
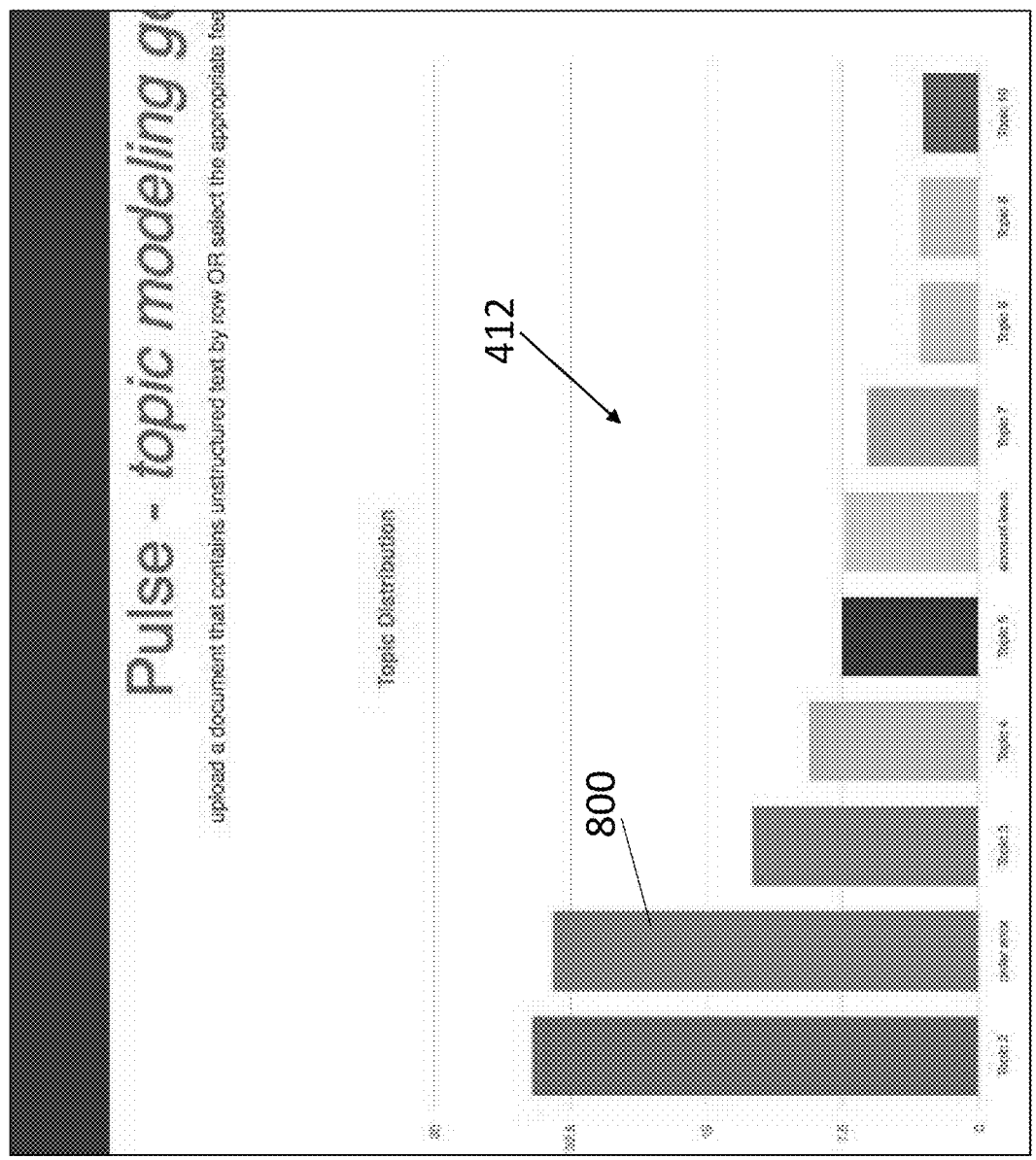
FIG. 8 illustrates another part of the interface shown in FIG. 4.
Figure 9:
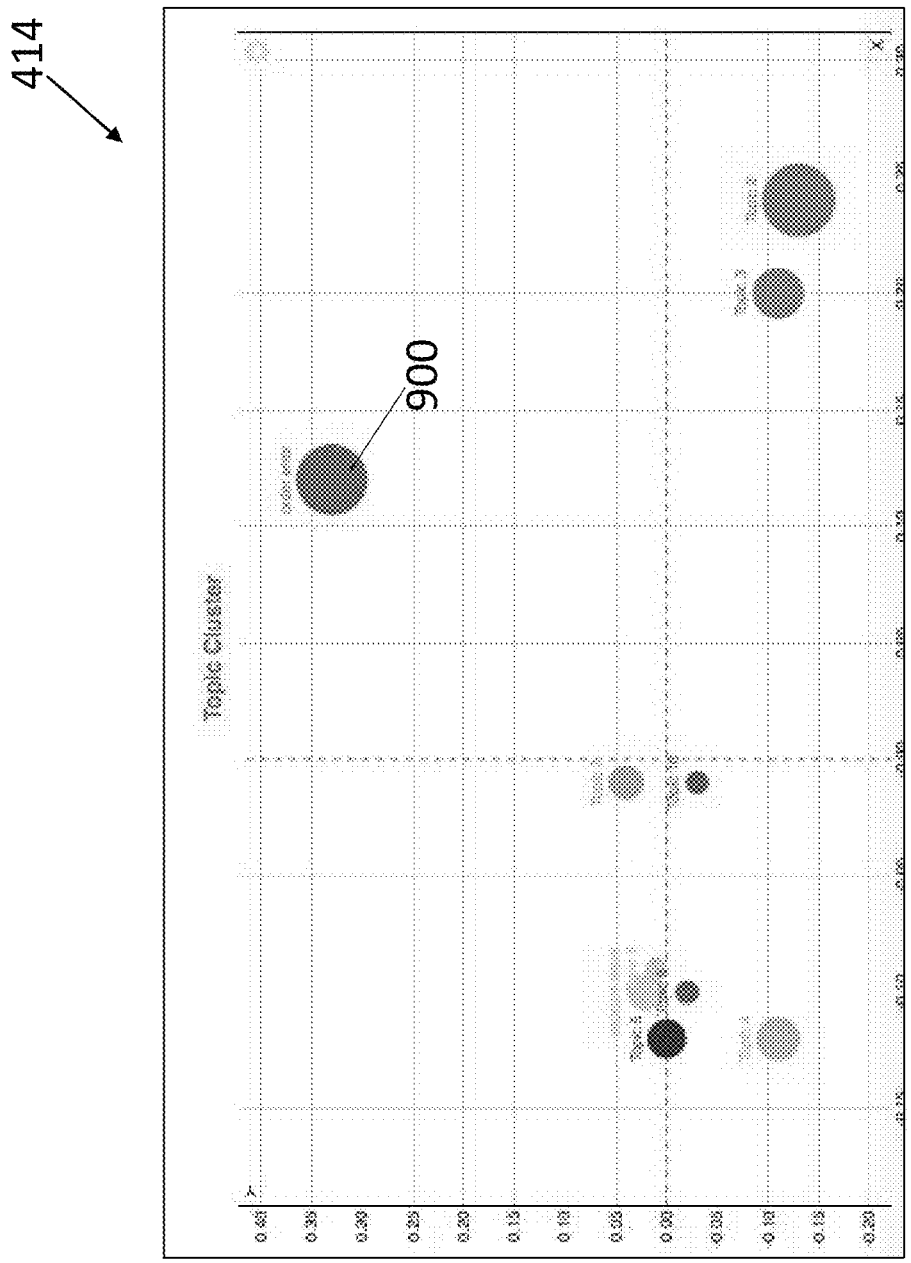
FIG. 9 illustrates another part of the interface shown in FIG. 4.

The topic groupings can initially be provided with first identifiers, such as generic names for the different groupings (e.g., Topic 1, Topic 2, and so on, as shown in FIG. 7). The user or operator can select a topic grouping using the data manager device 106 and can input a different name for the selected topic grouping into an input area 700. For example, the user can input a descriptive name (e.g., order error, account issue, etc.) for a selected topic grouping. The descriptive name can assist the user or operator in more readily identifying the concepts included in the feedback data associated with or included in that topic grouping. FIG. 7 illustrates the user or operator selecting the fourth topic grouping of the machine model and re-naming this topic grouping as customer service to indicate that the concepts in the feedback data associated with the fourth topic grouping relate to feedback regarding customer service.

The word cloud 408 (shown in FIGS. 4 and 6) depicts relative frequencies of use or prevalence of the words, phrases, and/or terms of interest in the topic grouping selected by the user or operator (e.g., from the drop-down list 702 shown in FIG. 7). Words, terms, or phrases of interest that appear larger in the word cloud 408 appear more often in the portion of the feedback data associated with the selected topic grouping than other words, terms, or phrases of interest occurring less often. The word cloud 408 provides the user or operator with a quick representation of the words or phrases appearing most often in the feedback data associated with the selected topic grouping.

In one embodiment, the words or phrases appearing in the word cloud 408 can be displayed in distinct colors, fonts, or the like, based on the connotation associated with the word or phrase. For example, words or phrases appearing in the feedback data that are associated with negative connotations (e.g., "website not working," "app broken," "wait time too long," etc.) can be presented in the word cloud 408 in red font, words or phrases appearing in the feedback data that are associated with positive connotations (e.g., "website working great," "friendly staff," etc.) can be presented in the word cloud 408 in green font, and words or phrases having neither negative nor positive connotations can be presented in the word cloud 408 in grey font.

The feedback data details list 410 (shown in FIGS. 4 and 6) lists different feedback datum in the feedback data associated with the topic grouping selected in the drop-down list 702 shown in FIG. 7. Each different feedback datum within the feedback data can be separately listed in the list 410, as shown in FIGS. 4 and 6. The words, phrases, and/or terms of interest can be highlighted or otherwise presented in a different manner for easier recognition of the user or operator of the data manager device 106. The feedback data that is displayed in the list 410 can have the confidential information removed or replaced with contextual placeholders (described above), thereby allowing the user or operator to read through the feedback data that includes the phrases and/or words of interest without reading confidential information.

The topic grouping histogram 412 (shown in FIGS. 5 and 8) visually represents relative prevalence of the feedback data among the different topic groupings. Each topic grouping can be provided with a different histogram bar 800, with the height of each bar 800 indicative of the amount of feedback data in the associated topic grouping relative to other topic groupings. The generic or descriptive name can be shown below the corresponding bar 800 to assist the user or operator in determining which topic groupings have more or less feedback data than other topic groupings. The histogram 412 allows the user or operator to visualize which topic groupings have more feedback from customers or clients of the pharmacy benefit manager. This can assist the user or operator in prioritizing which problems or issues to resolve more quickly than other problems or issues.

The topic cluster graph 414 (shown in FIGS. 4 and 9) visually indicates the relative amounts and relationships between the feedback data in the different topic groupings. Circles or clusters 900 represent the different topic groupings. Larger clusters 900 indicate that there are feedback data associated with the corresponding topic grouping, while smaller clusters 900 indicate that there is less feedback data in the associated topic grouping. The horizontal and vertical separations between the clusters 900 indicate how closely the concepts in the different clusters 900 are related. For example, clusters 900 that are closer together along the horizontal and/or vertical axes may have concepts that are more related than the concepts of other clusters 900 (yet are still included in different clusters 900). The data manager device 106 can determine that clusters 900 are to be closer together when the feedback data in one cluster 900 overlaps with the feedback data in another cluster 900 during one or more iterations of learning the relationships between or among feedback data.

Figure 10:
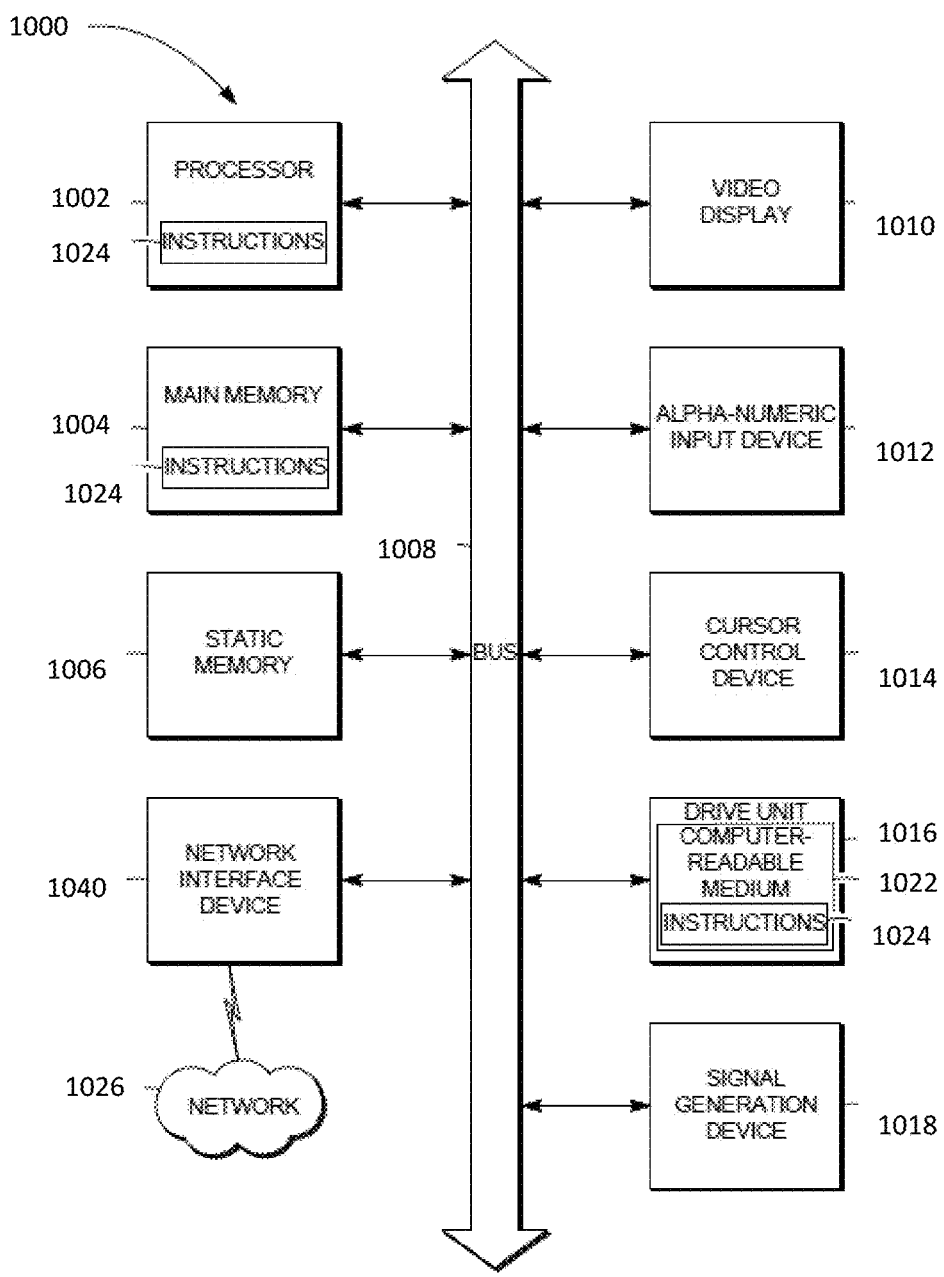
FIG. 10 shows a block diagram of a machine in the example form of a computer system within which a set of instructions may be executed causing the machine to perform anyone or more than one of the methods, processes, operations, or methodologies discussed herein.

FIG. 10 shows a block diagram of a machine in the example form of a computer system 1000 within which a set of instructions may be executed causing the machine to perform anyone or more than one of the methods, processes, operations, or methodologies discussed herein. The one or more than one of the devices 102, 106, 110, 112 may include the functionality of the one or more than one of the computer systems 1000.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or a machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform anyone or more of the methodologies discussed herein. Any machine loaded with the instructions is a dedicated machine for executing the present methods.

The example computer system 1000 includes a processor or more than one processor 1002 (e.g., a central processing unit (CPU) a graphics processing unit (GPU) or both), a main memory 1004, and a static memory 1006, which communicate with each other via a bus 1008. The memories 1004, 1006 are configured to store machine instructions for executing the methods and processes as described herein. The processor 1002 can be discrete components to execute the methods described herein, a programmable logic array loaded with instructions for the methods described herein, an integrated circuited loaded with the instructions for methods described herein. Accordingly, the processor or processors 1002 are dedicated to the methods described herein according to an embodiment. The computer system 1000 further includes a video display unit 1010 (e.g., a liquid crystal display, cathode ray tube, touchscreen, etc.). The computer system 1000 also includes an alphanumeric input device 1012 (e.g., a keyboard), a cursor control device 1014 (e.g., a mouse), a drive unit 1016, a signal generation device 1018 (e.g., a speaker) and a network interface device 1020.

The drive unit 1016 includes a computer-readable medium 1022 on which is stored one or more sets of instructions (e.g., software 1024) embodying anyone or more of the methodologies or functions described herein. The software 1024 may also reside, completely or at least partially, within the main memory 1004 and/or within the processor 1002 during execution thereof by the computer system 1000, the main memory 1004 and the alphanumeric input device 1012 also constituting computer-readable media. The software 1024 may further be transmitted or received over a network 1026 via the network interface device 1020.

While the computer-readable medium 1022 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform anyone or more of the methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect other elements beyond those explicitly recited.

Certain systems, apparatus, applications or processes are described herein as including several modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. As used herein, "a" or "an" may reflect a single part or multiple parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies. Thus, systems and methods for pharmacy messaging have been described. Although embodiments of the present disclosure have been described with reference to specific example embodiments, it will be evident that various modifications and changes may be made to these embodiments without departing from the broader spirit and scope of the embodiments of the disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
    receiving a topic model number that defines how many different topic groups are to be created by an organizational machine model and used to organize feedback data from one or more sources into the different topic groups based on similarities in concepts expressed in the feedback data;
    receiving a hyperparameter optimization alpha value that defines how likely a feedback datum in the feedback data is to be included in a single topic group of the different topic groups;
    receiving a hyperparameter optimization beta value that defines how broadly each of the different topic groups are defined relative to the feedback data;
    receiving a training iteration value that defines a number of training iterations to be used in machine learning to associate portions of the feedback data with different combinations of the topic groups;
    using machine learning to train the organizational machine model using the topic model number, the hyperparameter optimization alpha value, the hyperparameter optimization beta value, the training iteration value, and the feedback data, the organizational machine model trained by defining different relationships between selected concepts for each of the training iterations, wherein, for each iteration of the training iterations, the feedback data is transformed by sorting the portions of the feedback data having at least one of the relationships with each other into the same topic group of the topic groups based on the topic model number, the hyperparameter optimization alpha value, and the hyperparameter optimization beta value; and
    creating one or more software applications to include the organizational machine model that is trained, the one or more software applications configured to subsequently sort the portions of the feedback data and updates to the feedback data among the different topic groups according to the organizational machine model.

2. The method of claim 1, wherein the organizational machine model is trained using a defined default parameter for the topic model number, and further comprising:
    receiving a modified topic model number; and
    revising the organizational machine model using the modified topic model number such that the organizational machine model organizes the portions of the feedback data into a different number of the topic groups.

3. The method of claim 1, wherein the organizational machine model is trained to automatically identify the different topic groups of the feedback data that was provided to a service provider from one or more data sources based on similarities in concepts conveyed in the feedback data.

4. The method of claim 1, wherein the organizational machine model is trained to automatically update the topic groups into which the feedback data is organized as updated, new, or different feedback data is provided from one or more data sources.

5. The method of claim 1, further comprising:
receiving an ontology selection that designates whether individual identifying information is removed from the feedback data provided to a service provider from one or more data sources.

6. The method of claim 1, further comprising generating a user interface on a display based on the organizational machine model to visually represent distribution of the portions of the feedback data into the different topic groups.

7. The method of claim 6, wherein the user interface that is generated visually presents a distribution of service provider feedback data among the different topic groups, a cluster diagram of contents of the feedback data in the different topic groups, a word cloud of the feedback data in a selected topic group of the topic groups, a list of the feedback data in the selected topic group, or a combination of two or more of the distribution, the cluster diagram, the word cloud, or the list.

8. A tangible and non-transitory computer-readable storage medium comprising instructions that direct one or more computer processors to:
receive a topic model number that defines how many different topic groups are to be created by an organizational machine model and used to organize feedback data from one or more sources into the different topic groups based on similarities in concepts expressed in the feedback data;
receive a hyperparameter optimization alpha value that defines how likely a feedback datum in the feedback data is to be included in a single topic group of the different topic groups;
receive a hyperparameter optimization beta value that defines how broadly each of the different topic groups are defined relative to the feedback data;
receive a training iteration value that defines a number of training iterations to be used in machine learning to associate portions of the feedback data with different combinations of the topic groups;
apply machine learning to train the organizational machine model using the topic model number, the hyperparameter optimization alpha value, the hyperparameter optimization beta value, the training iteration value, and the feedback data, the organizational machine model trained by defining different relationships between selected concepts for each of the training iterations, wherein, for each iteration of the training iterations, the feedback data is transformed by sorting the portions of the feedback data having at least one of the relationships with each other into the same topic group of the topic groups based on the topic model number, the hyperparameter optimization alpha value, and the hyperparameter optimization beta value; and
create one or more software applications to include the organizational machine model that is trained, the one or more software applications configured to subsequently sort the portions of the feedback data and updates to the feedback data among the different topic groups according to the organizational machine model.

9. The computer-readable medium of claim 8, wherein the instructions direct the one or more processors to train the organizational machine model using a defined default parameter for the topic model number, the instructions also directing the one or more processors to:
receive a modified topic model number; and
revise the organizational machine model using the modified topic model number such that the organizational machine model organizes the portions of the feedback data into a different number of the topic groups.

10. The computer-readable medium of claim 8, wherein the organizational machine model is trained to automatically identify the different topic groups of the feedback data that was provided to a service provider from one or more data sources based on similarities in concepts conveyed in the feedback data.

11. The computer-readable medium of claim 8, wherein the organizational machine model is trained to automatically update the topic groups into which the feedback data is organized as updated, new, or different feedback data is provided from one or more data sources.

12. The computer-readable medium of claim 8, wherein the instructions direct the one or more processors to receive an ontology selection that designates whether individual identifying information is removed from the feedback data provided to a service provider from one or more data sources.

13. The computer-readable medium of claim 8, wherein the instructions also direct the one or more processors to generate a user interface on a display based on the organizational machine model to visually represent distribution of the portions of the feedback data into the different topic groups.

14. The computer-readable medium of claim 13, wherein the user interface that is generated visually presents a distribution of service provider feedback data among the different topic groups, a cluster diagram of contents of the feedback data in the different topic groups, a word cloud of the feedback data in a selected topic group of the topic groups, a list of the feedback data in the selected topic group, or a combination of two or more of the distribution, the cluster diagram, the word cloud, or the list.

15. A system comprising:
a data manager device that includes one or more processors configured to receive feedback data containing medial information from plural different sources via one or more computer networks, the one or more processors of the data manager device configured to receive a topic model number that defines how many of different topic groups are to be created by an organizational machine model and used to organize the feedback data, the one or more processors configured to receive a hyperparameter optimization alpha value that defines how likely a feedback datum in the feedback data is to be included in a single topic group of the different topic groups, the one or more processors configured to receive a hyperparameter optimization beta value that defines how broadly each of the different topic groups are defined relative to the feedback data,
wherein the one or more processors of the data manager device are configured to receive a training iteration value that defines a number of training iterations to be used in machine learning to associate portions of the feedback data with different combinations of the topic groups, the one or more processors configured to use machine learning to train the organizational machine model using the topic model number, the hyperparameter optimization alpha value, the hyperparameter optimization beta value, the training iteration value, and the feedback data, the one or more processors configured to train the organizational machine model by defining different relationships between selected concepts for each of the training iterations, wherein, for each iteration of the training iterations, the feedback data is transformed by sorting the portions of the feedback data having at least one of the relationships with each other into the same topic group of the topic groups based on the topic model number, the hyperparameter optimization alpha value, and the hyperparameter optimization beta value, wherein the one or more processors are configured to create one or more software applications to include the organizational machine model that is trained, the one or more software applications configured to subsequently sort the portions of the feedback data and updates to the feedback data among the different topic groups according to the organizational machine model.

* * * * *